Nov. 22, 1960 H. C. SWIM Plant Pat. 1,988
CAMELLIA PLANT
Filed Dec. 7, 1959
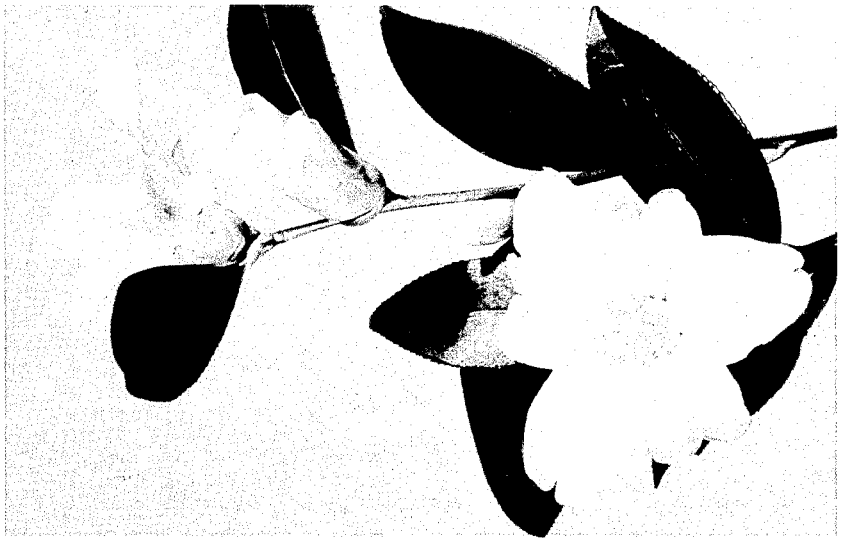
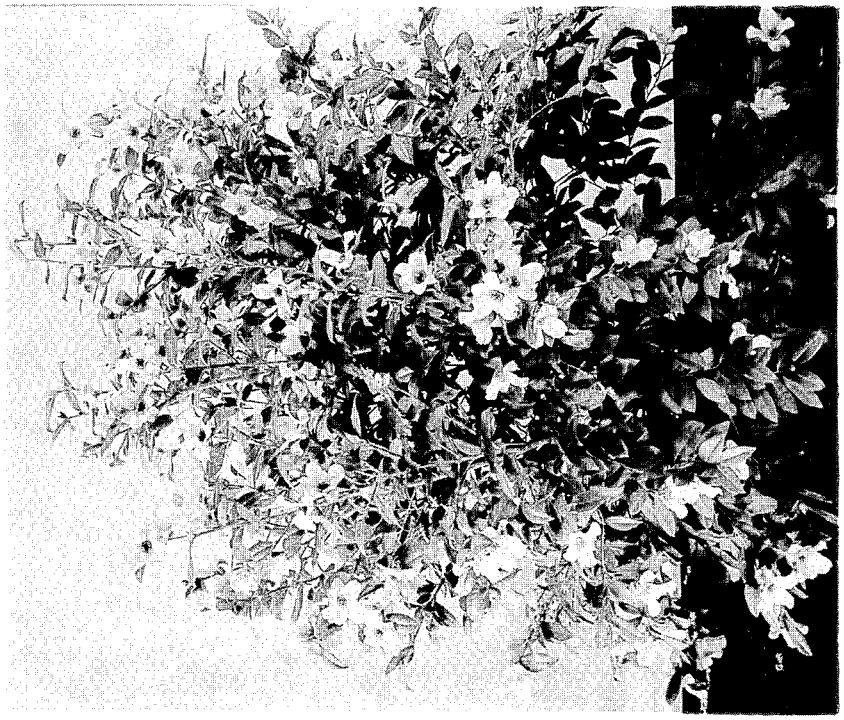
Inventor.
H. C. Swim
By: Robb & Robb
Attorneys.

United States Patent Office

Plant Pat. 1,988
Patented Nov. 22, 1960

1,988

CAMELLIA PLANT

Herbert C. Swim, Ontario, Calif., assignor to Armstrong Nurseries, Inc., Ontario, Calif., a corporation of California Filed Dec. 7, 1959, Ser. No. 858,004

1 Claim. (Cl. 47—60)

The present invention relates to a new and distinct variety of camellia plant which was originated by me by crossing one of the varieties of *Camellia japonica* known as "Lady Vansittart" (unpatented) with another unnamed and unpatented variety of the species *Camellia saluenensis.*

The primary objective of this breeding was to produce an improved camellia which combines the floriferousness, well-branching habit and sun-hardiness of the unnamed pollen parent of the species *C. saluenensis,* with the larger and more attractive foliage and larger flowers of the seed parent, "Lady Vansittart." This objective was fully achieved, along with other desirable improvements, as evidenced by the following unique combination of characteristics which are outstanding in my new camellia variety and which distinguish it from its parents, as well as from all other varieties of which I am aware:

(1) A vigorous, upright, well-branched, and relatively compact plant habit;

(2) Attractive dark green glossy foliage, ranging in size from small to medium;

(3) Relatively good sun-hardiness under conditions where reasonable soil moisture is maintained at all times, as evidenced by the fact that plants of my new variety grown in southern California have withstood temperatures as high as 105° to 110° F. for periods of several days, without undue yellowing of the foliage by sunburn, thereby representing a definite improvement over previously known *C. japonica* varieties;

(4) A very floriferous habit, with the flowers borne laterally on many shoots, as well as borne terminally;

(5) A relatively precocious blooming habit, as evidenced by the fact that the plants bloom well while still quite small and young, in contrast to the usual habit of most *C. japonica* varieties;

(6) The single form of the flowers, with each flower consisting essentially of six petals arranged in two imbricated layers of three petals each, and with the petals of the outer layer somewhat shorter than the others, thereby presenting an interesting and attractive flower form;

(7) A distinctive and attractive pale pink general color tonality of the flowers;

(8) A blooming period ranging from midseason to late, and extending over a period of two months or more; and (9) A habit of cleanly dropping the old flowers in their individual entireties.

The seed parent, "Lady Vansittart," of my new camellia is a variety of *C. japonica,* and is characterized by having an upright and vigorous plant habit, with attractive, glossy, lanceolate, dark green foliage. Its flowers are semi-double and range to 10 or 11 cm. in width and approximately one-half this dimension in depth, when fully expanded, with the flower form quite regular, generally symmetrical and imbricated, and having the central stamens showing very readily. The flowers of the particular seed parent used in breeding the present new camellia were dark pink in color, although other plants of "Lady Vansittart" sometimes bear flowers varying from nearly white to a darker red. In comparison with the seed parent, my new camellia is differentiated therefrom by having a more branching habit; the foliage is considerably smaller than that of this parent; the new variety is much more sun-hardy, whereas this seed parent is not sun-hardy; the new variety is considerably more floriferous, and its flowers are borne laterally quite commonly, whereas those of this parent are not; the flowers of the new variety are single in form and pale pink in color, whereas those of the seed parent are semi-double in form and dark pink in color; and the flowers of the new variety are somewhat smaller than those of this parent.

The unnamed pollen parent of my new variety, which was a form of *C. saluenensis,* is a more or less semi-spreading to spreading plant of compact bushy form, well-branched, and with very small leaves. It was further characterized by a very floriferous habit, with the flowers ranging about 4 or 5 cm. wide, said flowers being of single form and having 6 or 7 petals, and the flowers being very pale pink or near white in color. In contrast to this parent, my new variety is quite upright in habit; the foliage is considerably larger; the flowers are also larger; and although the flowers are pale pink in color, they are somewhat darker than the color of the flowers of the pollen parent.

Asexual reproduction of my new variety by both graftings and cuttings, as performed at Ontario, California, shows that the foregoing characteristics and distinctions come true to form in my new camellia and are established and transmitted through succeeding propagations.

The accompanying drawing shows a typical specimen plant of my new camellia variety as depicted in black-and-white to indicate primarily its general form and habits of growth, as well as typical specimens of the flowers and foliage in different stages of development as depicted on an enlarged scale and in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway") as indicated:

Type: Ornamental; flowering evergreen shrub; for general landscape use and for cut flowers.

Class: *Japonica* × *saluenensis* hybrid.

Breeding: Seedling.

*Seed parent.*—"Lady Vansittart."

*Pollen parent.*—An unnamed variety of the species "*C. saluenensis.*"

Propagation: Holds its distinguishing characteristics through succeeding propagations by both grafting and cuttings.

*Plant*

Habit: Bushy; upright; much-branched; relatively compact.

Vigor: Medium.

New stems: Slender; glabrous. Color—near Absinthe Green, Plate XXXI (Ridgway).

Older stems: Glabrous; bark becomes fissured and scurfy. Color—near Cinnamon Brown, Plate XV (Ridgway).

Mature branches: Rough and scurfy when one or two years old, becoming more smooth as original bark is sloughed off. Color—between Drab-Gray, Plate XLVI (Ridgway) and Light Grayish Olive, Plate XLVI (Ridgway).

Leaves:

*Habit.*—Abundant; borne alternately.

*Texture.*—Leathery.

*Size.*—From small to medium in comparison with average size for usual varieties of *C. japonica.* Width—from 3 to 5 cm. Length—from 6 to 10 cm.

*Petiole.*—Medium caliper; from 4 to 10 mm. long; with shallow groove along upper surface; almost glabrous and with slight pubescence, particularly along margins of groove.

*Shape.*—From oval to lanceolate. Apex—usually acute, but sometimes acuminate. Base—usually acute, but sometimes obtuse. Margin—simply serrate, except lower ¼ or ⅓ toward base is usually entire.

*Upper surface.*—Glossy. Color: mature leaves—between Cossack Green, Plate VI (Ridgway) and Empire Green, Plate XXXII (Ridgway); young leaves—near Cress Green, Plate XXXI (Ridgway). Veins—lighter in color.

*Lower surface.*—Glossy. Color: mature leaves—near Light Elm Green, Plate XVII (Ridgway); young leaves—between Courge Green, Plate XVII (Ridgway) and Biscay Green, Plate XVII (Ridgway). Veins—darker in color.

*Flower*

Flowers borne: Sessile; terminal or axillary; usually singly, but often doubly when terminal.

Quantity of bloom: Abundant.

Time of bloom: One season; from about mid-February to about mid-April at Ontario, California.

Fragrance: None.

Bud:

*Size.*—Medium.

*Form.*—Slender; pointed.

*Sepals.*—Numerous; usually from 6 to 9 in number; increasing in size from the outermost which are nearly round, to the innermost, which are broadly obovate. Outside surface—pubescent; color—near Rainette Green, Plate XXXI (Ridgway). Inside surface—glabrous; color—near Absinthe Green, Plate XXXI (Ridgway).

*Opening.*—Opens up well.

Bloom:

*Size (when fully open).*—Medium; from 7 to 9 cm.

*Petalage.*—Single; 6 or 7 petals, without petaloids; seventh petal is usually reduced in size and is more a sepal than a petal.

*Form.*—Usually arranged in two imbricated layers, with the three outer petals often ranging up to one cm. shorter than the three inner petals; all petals usually reflexed outward and greatest at the apex; newly opened flowers are cup-shaped, later becoming more bell-shaped to flat at maturity.

*Petals.* — Thickness — moderate. Surfaces — shiny, both inside and outside. Shape—oval; usually with one notch at apex.

*Color.*—Newly opened flower—Outer petals: outside surface—near Rose Madder, Plate 23/3, page 23 (Wilson), with area in center of petal from apex toward base near Carmine, Plate 21/1, page 21 (Wilson), and with occasional vegetative streak near apex of near Lemon Yellow, Plate 4/3, page 4 (Wilson); inside surface—between Rose Madder, Plate 23/3, page 23 (Wilson) and Tyrian Rose, Plate 24/3, page 24 (Wilson), with occasional vegetative streak near apex of near Lemon Yellow, Plate 4/3, page 4 (Wilson). Inner petals: outside surface—near Phlox Pink, Plate 625/3, page 77 (Wilson); inside surface—near Fuchsine Pink, Plate 627/3, page 78 (Wilson). 2–3 days open flower — Outer petals: outside surface—near Rose Madder, Plate 23/3, page 23 (Wilson), with area in center of petal from apex toward base near Carmine, Plate 21/1, page 21 (Wilson), and with occasional vegetative streaks near apex of near Lemon Yellow, Plate 4/3, page 4 (Wilson); inside surface—near Phlox Pink, Plate 625/3, page 77 (Wilson), with occasional vegetative streaks near apex near Lemon Yellow, Plate 4/3, page 4 (Wilson). Inner petals: outside surface — near Fuchsine Pink, Plate 627/3, page 78 (Wilson); inside surface—near Persian Rose, Plate 628/3, page 149 (Wilson).

*General color effect.*—Newly opened flower — near Fuchsine Pink, Plate 627/3, page 78 (Wilson). 2–3 days open flower—near Persian Rose, Plate 628/3, page 149 (Wilson).

*Behavior.*—Flowers persist on plant until they become old and then drop off cleanly as entire flower.

*Longevity.*—On bush in garden—from 3 to 5 days in February. Cut flowers grown outdoors and kept at room temperature—2 or 3 days.

*Reproductive organs*

Stamens: Up to from 60 to 70 in number; from 5 to 15 mm. in length; most with anthers; outer filaments united at base equal to from ¼ to ½ their length.

*Color of filament.*—Near Shell Pink, Plate 516/3, page 135 (Wilson).

*Color of anthers.*—Newly opened flower — margins near Indian Yellow, Plate 6, page 6 (Wilson), with remainder near Shell Pink, Plate 516/3, page 135 (Wilson). 2–3 days open flower — margins near Mahogany Red, Plate II (Ridgway), with remainder near Shell Pink, Plate 516/3, page 135 (Wilson).

Pistils: One; about 2 or 3 cm. long; style divided into three arms at apex for ¼ to ½ its length. Color—near Chartreuse Green, Plate 663/3, page 90 (Wilson).

Seeds: None produced at Ontario, California.

I claim:

A new and distinct variety of camellia plant, substantially as herein shown and described, characterized particularly as to novelty by the unique combination of a vigorous, upright, well-branched, relatively compact plant habit, attractive dark green glossy foliage, ranging in size from small to medium, good sun-hardiness, a very floriferous habit, with the flowers borne both laterally on many shoots and terminally, a relatively precocious blooming habit, the single form of the flowers, said flowers essentially having six petals each, with the petals of the outer layer being somewhat shorter than the others, a distinctive pale pink general color tonality of the flowers, a blooming period ranging from midseason to late and extending over a period of approximately two months or more, and a habit of dropping the old flowers cleanly in their respective entireties.

No references cited.